United States Patent [19]
Clark et al.

[11] Patent Number: 5,686,407
[45] Date of Patent: Nov. 11, 1997

[54] HEPATOCYTE GROWTH FACTOR TO TREAT GLAUCOMA

[75] Inventors: Abbot F. Clark, Arlington; Robert J. Wordinger, Euless, both of Tex.

[73] Assignee: Alcon Laboratories, Inc., Fort Worth, Tex.

[21] Appl. No.: 515,663

[22] Filed: Aug. 16, 1995

[51] Int. Cl.⁶ ..................................................... A61K 38/00
[52] U.S. Cl. .................................................. 514/2; 514/913
[58] Field of Search ........................................ 514/2, 913

[56] References Cited

U.S. PATENT DOCUMENTS 5,589,451  12/1996  Wilson ......................................... 514/2

OTHER PUBLICATIONS

Boros, et al., *The Lancet*, Hepatocyte growth factor: a multifunctional cytokine, 345, 293–295 (Feb. 4, 1995).

Rosen, et al., *The Journal of Cell Biology*, Scatter Factor and the c–Met Receptor: A Paradigm for Mesenchymal/Epithelial Interaction, vol. 127, No. 6, Part 2, 1783–1787 (Dec., 1994).

Wilson, et al., *Exp. Eye Res.*, Effect of Epidermal Growth Factor, Hepatocyte Growth Factor, and Keratinocyte Growth Factor, on Proliferation, Motility and Differentiation of Human Corneal Epithelial Cells, 59, 665–678 (1994); and.

Clark, et al., *Investigative Ophthalmology & Visual Science*, Glucocorticoid–Induced Formation of Cross–Linked Actin Networks in Cultured Human Trabecular Meshwork Cells, 35:1, 281–294 (Jan. 1994).

Lyon, et al., *Biochemical Society Transactions*, Hepatocyte Growth Factor/Scatter Factor: A Heparan Sulphate–Binding Pleiotropic Growth Factor, vol. 22, No. 2, 365–370 (1994); and.

Vigna, et al., *Cellular and Molecular Biology*, Hepatocyte Growth Factor and Its Recetor, the Tyrosine Kinase Encoded by the c–Met Proto–Oncogene, vol. 40, No. 5, 597–604 (1994).

*Primary Examiner*—Raymond Henley, III
*Attorney, Agent, or Firm*—Sally Yeager

[57] ABSTRACT

Methods for controlling IOP with compositions of HGF Receptor Activators are disclosed.

3 Claims, 1 Drawing Sheet

HEPATOCYTE GROWTH FACTOR TO TREAT GLAUCOMA

BACKGROUND OF THE INVENTION

The present invention relates to the field of ophthalmology and more specifically to the field of glaucoma therapy.

Glaucoma is a group of heterogeneous diseases which are characterized by the progressive loss of vision due to glaucomatous optic neuropathy. This optic neuropathy involves cupping of the optic nerve head and the gradual destruction of retinal ganglion cells. One of the most important risk factors for the development of glaucoma is elevated intraocular pressure (IOP). The elevated IOP associated with glaucoma is thought to contribute to the optic nerve head cupping and the eventual destruction of the optic nerve. This elevated IOP is due to a blockage of aqueous humor outflow at the trabecular meshwork located at the iridocorneal angle of the anterior segment of the eye. Aqueous humor is continuously made by the ciliary body and provides nutrients to the avascular tissues of the anterior segment of the eye. Aqueous humor exits the eye by percolating through a reticulated tissue known as the trabecular meshwork, into the canal of Schlemm, and into the venous circulation. The trabecular meshwork imparts a resistance to aqueous outflow which is necessary to maintain the shape of the eye. However, in many forms of glaucoma, an increased resistance to aqueous outflow develops which is responsible for the generation of ocular hypertension (i.e. elevated IOP). A number of investigators have studied the morphological and biochemical changes which occur in the glaucomatous trabecular meshwork. Two of the most important findings are a loss of trabecular meshwork cells and the accumulation of extracellular material, especially in the trabecular meshwork tissue adjacent to the canal of Schlemm where the major site of outflow resistance resides.

Current glaucoma therapy attempts to lower the elevated IOP associated with glaucoma and thereby reduce a major risk factor for the pathogenesis of glaucoma. A variety of pharmacologic agents are used in glaucoma therapy. Beta-adrenergic antagonism (β-blockers) and carbonic anhydrase inhibitors lower IOP by suppressing aqueous humor formation. Sympathomimetics appear to stimulate trabecular outflow by an as yet undefined mechanism. Miotics indirectly increase aqueous outflow by contracting the ciliary muscle and thereby altering the geometry of the trabecular meshwork. All of these agents only indirectly treat a symptom of the disease, and often times do not sufficiently lower the IOP to totally halt progression of the disease.

There are two additional therapeutic means for treating glaucoma. In glaucoma filtration surgery, a small piece of tissue in the aqueous outflow pathway is excised forming a channel for aqueous humor to exit the eye through a "filtering bleb" which is a fistula between the anterior chamber and sub-Tenon's space in the sclera. Filtration surgery can lead to dramatic IOP reductions in some patients. However, filtration surgery also has the potential for the development of hypotony (i.e. "soft eye" due to too much pressure lowering), and in most cases, the surgical filter eventually fails due to a scar-induced sealing of the filtration bleb. A second surgical method involves trabeculoplasty in which an argon laser is used to make a number of thermal burns in the glaucomatous trabecular meshwork. A current theory for trabeculoplasty-induced IOP lowering is that the laser burn causes the release of a mediator which stimulates the proliferation of TM cells and remodels the entire trabecular meshwork leading to improved aqueous outflow. Although initially successful in a large number of treated glaucoma patients, trabeculoplasty appears to lose its effectiveness with time, and patients often require repeated treatment or further pharmaceutical therapy.

There is a need for a therapy which reverses and halts the glaucomatous changes in the trabecular meshwork and which provides long lasting IOP control. The present invention provides a glaucoma therapy which addresses this need.

SUMMARY OF THE INVENTION

The present invention provides a method for treating and/or preventing the elevated IOP associated with glaucoma. The method involves the administration to the anterior segment of the eye a composition containing an HGF Receptor Activator (defined below).

DESCRIPTION OF PREFERRED EMBODIMENTS

Figure 1:
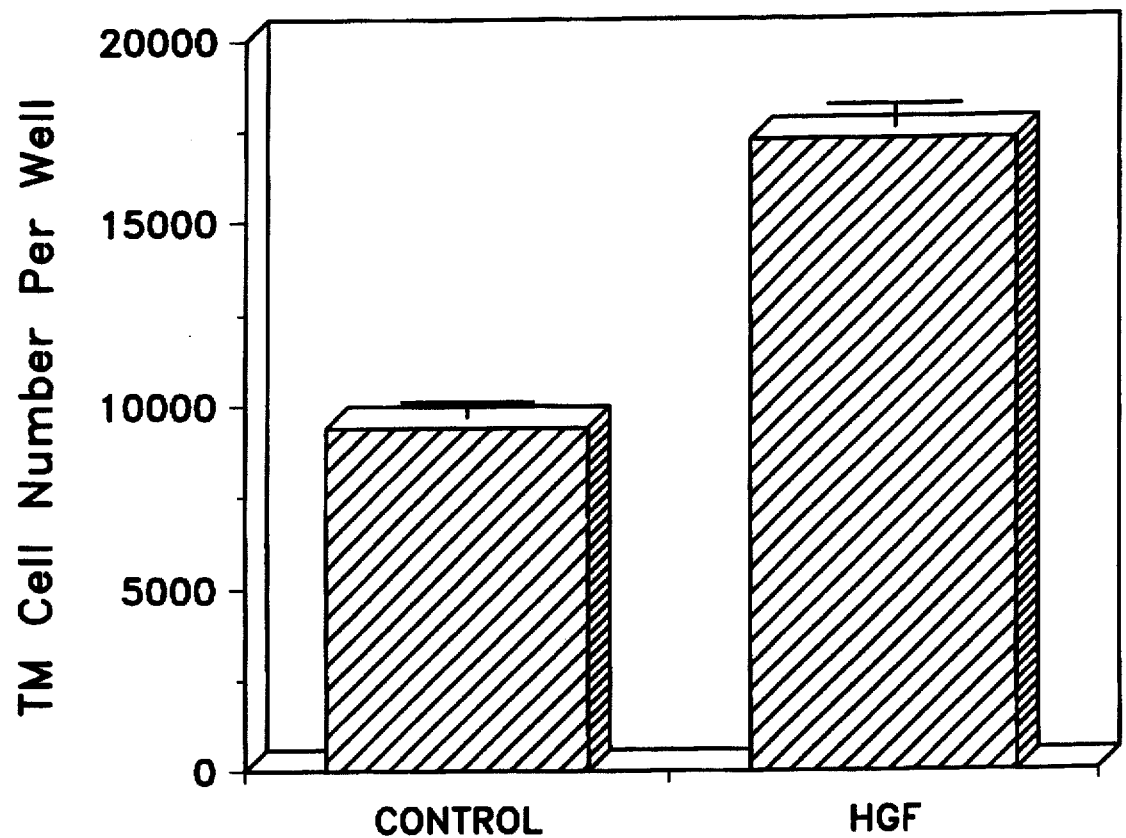
FIG. 1 shows the effect of HGF on trabecular meshwork cell growth.

HGF is a pleiotropic factor, found in a variety of cells and tissues including the liver, spleen, kidney, and adrenal glands, whose biological role is not completely understood. Until now, it has not been found in trabecular meshwork cells. It has been shown to regulate cell growth, development, mobility, and morphogenesis, see Boros, et al., *The Lancet*, Hepatocyte growth factor: a multifunctional cytokine, 345, 293–295 (Feb. 4, 1995). HGF, also known as scatter factor, may mediate interactions between mesenchyme and epithelia during embryogenesis, organ repair, and neoplasia, Rosen, et al., *The Journal of Cell Biology*, Scatter Factor and the c-Met Receptor: A Paradigm for Mesenchymal/Epithelial Interaction, Vol. 127, No. 6, Part 2, 1783–1787 (December, 1994). At least one ophthalmic cell type (corneal epithelial cells) has been shown to respond to HGF, Wilson, et al., *Exp. Eye Res.*, Effect of Epidermal Growth Factor, Hepatocyte Growth Factor, and Keratinocyte Growth Factor, on Proliferation, Motility and Differentiation of Human Corneal Epithelial Cells, 59, 665–678 (1994).

Although not bound by any theory, it is believed that the delivery of HGF Receptor Activators to a glaucomatous trabecular meshwork induces proliferation of the trabecular meshwork cells, which "normalizes" the aqueous outflow facility thereby lowering IOP. Well controlled IOP should halt or possibly reverse glaucomatous optic neuropathy.

Any agent which activates the hepatocyte growth factor receptor ("HGF Receptor Activators") is included within the purview of this invention. Hepatocyte growth factor (HGF) is the natural ligand for the HGF receptor. HGF mimetics as well as other small molecular weight ligands which interact with the HGF receptor are included with HGF within the definition of HGF Receptor Activators of the present invention.

HGF Receptor Activators are useful in treating glaucoma by lowering and controlling elevated IOP. The HGF Receptor Activators are administered to the anterior chamber of a glaucomatous mammalian eye in an amount and at a frequency such that the elevated IOP is lowered and controlled. The mode of administration (topical versus intraocular injection) and the dosing regimen will depend on the characteristics of the individual HGF Receptor Activator, such as its potency and its solubility, stability, and bioavailability.

Typically the HGF Receptor Activators will be administered once daily at a concentration of 0.005–1% according to the discretion of a skilled clinician.

EXAMPLE 1

Topical Ocular Solution

| | Amount (wt %) |
|---|---|
| HGF Mimetic | 0.001–1.0 |
| Tyloxapol | 0.01 to 0.05 |
| HPMC | 0.5 |
| Benzalkonium chloride | 0.01 |
| Sodium chloride | 0.8 |
| Edetate disodium | 0.01 |
| NaOH/HCl | q.s. pH 7.4 |
| Purified water | q.s. 100 ml |

EXAMPLE 2

Formulation for Sterile Introcular Injection

| Each mL contains: | |
|---|---|
| HGF | 1–500 ng |
| Sodium chloride | 7.14 mg |
| Potassium chloride | 0.38 mg |
| Calcium chloride dihydrate | 0.154 mg |
| Magnesium chloride dihydrate | 0.20 mg |
| Dried sodium phosphate | 0.42 mg |
| Sodium bicarbonate | 2.1 mg |
| Dextrose | 0.92 mg |
| NaOH/HCl | q.s. pH 7.2 |
| Purified water for injection | q.s. 1 mL |

EXAMPLE 3

Cultured human trabecular meshwork (TM) cells were grown as previously reported, Clark, et al., *Investigative Ophthalmology & Visual Science*, Glucocorticoid-Induced Formation of Cross-Linked Actin Networks in Cultured Human Trabecular Meshwork Cells, 35:1, 281–294 (January 1994). Briefly, trabecular meshwork tissue was carefully dissected from human donor eyes and placed in a single well of a 24 well plate in the presence of culture media [Ham's F10 media containing L-glutamine, antibiotics, and 10% fetal bovine serum]. The cells were passaged by the addition of Cytodex beads to confluent monolayers of cells; after 1 week, the cell-coated beads were transferred to a fresh culture dish using the same culture media. To evaluate the effects of HGF on TM cell proliferation, the TM cells were briefly trypsinized and counted using a Coulter counter. Ten thousand cells were plated into each well of a six well plate in assay media [Ham's F10 containing L-glutamine, antibiotics, and 0.5% fetal bovine serum]. HGF (5 ng/mL) was added to three wells while the other three wells served as untreated controls. The plate was placed in a humidified 37° C. incubator with an atmosphere of 7% $CO_2$/93% air for 2 weeks. The media in each well was exchanged with flesh assay media twice a week. At the end of two weeks, the cell number in each well was determined by trypshnizing the cultures and counting the cells in a Coulter counter. The cells exposed to HGF doubled during the two week period while the number of cells in the untreated control wells did not change over the course of two weeks (FIG. 1 ).

We claim:

1. A method for controlling IOP by administering to an affected eye a pharmaceutically effective amount of an HGF Receptor Activator.

2. The method of claim 1 wherein the HGF Receptor Activator is HGF.

3. The method of claim 1 wherein the HGF Receptor Activator is an HGF mimetic.

* * * * *

UNITED STATES PATENT AND TRADEMARK OFFICE
CERTIFICATE OF CORRECTION

PATENT NO. : 5,686,407

DATED : November 11, 1997

INVENTOR(S) : Clark, et al.

It is certified that error appears in the above-indentified patent and that said Letters Patent is hereby corrected as shown below:

On title page, item [73] should read as follows:
--Alcon Laboratories, Inc., and The University of North Texas Health Sciences Center.--

Signed and Sealed this

Fourteenth Day of July, 1998

Attest:

BRUCE LEHMAN

*Attesting Officer*  Commissioner of Patents and Trademarks